US005618004A

United States Patent [19]
Klearman et al.

[11] Patent Number: 5,618,004
[45] Date of Patent: Apr. 8, 1997

[54] TOP MOUNTED CUPS FOR STORING CRUSHING AND DISPENSING PILLS

[75] Inventors: Jeffrey Klearman, St. Louis; Jerry Roth, House Springs; Matt Roth; Robert T. Bronson, both of St. Louis, all of Mo.

[73] Assignee: Lake Medical Products, Inc., St. Louis, Mo.

[21] Appl. No.: 485,358

[22] Filed: Jun. 7, 1995

Related U.S. Application Data

[63] Continuation-in-part of Ser. No. 288,599, Aug. 10, 1994, Pat. No. 5,553,793, which is a continuation-in-part of Ser. No. 168,019, Dec. 15, 1993, Pat. No. 5,376,072.

[51] Int. Cl.$^6$ ..................................................... B02C 19/08
[52] U.S. Cl. ........................... 241/21; 241/30; 241/169.2; 241/199; 241/DIG. 27
[58] Field of Search ........................... 241/21, 30, 169.2, 241/199, DIG. 27

[56] References Cited

U.S. PATENT DOCUMENTS

| | | |
|---|---|---|
| 1,165,686 | 12/1915 | McElroy . |
| 2,392,595 | 6/1959 | Tupper . |
| 2,602,596 | 7/1952 | Jones et al. . |
| 3,915,393 | 10/1975 | Elkins . |
| 4,057,052 | 11/1977 | Kaufman et al. . |
| 4,209,136 | 6/1980 | Linden et al. . |
| 4,366,930 | 1/1983 | Trombetti, Jr. . |
| 4,568,331 | 2/1986 | Fischer et al. . |
| 4,715,854 | 12/1987 | Vaillancourt . |
| 4,765,549 | 8/1988 | Sherman . |
| 4,976,971 | 11/1990 | Smith ...................................... 241/169 |
| 5,067,666 | 11/1991 | Sussman . |
| 5,118,021 | 6/1992 | Fiocchi . |
| 5,148,995 | 9/1992 | Hurst . |
| 5,322,227 | 6/1994 | Fiocchi . |
| 5,376,072 | 12/1994 | Klearman et al. .......................... 604/82 |
| 5,533,683 | 7/1996 | Fay et al. ................................. 241/169 |
| 5,553,793 | 9/1996 | Klearman et al. .......................... 241/30 |

OTHER PUBLICATIONS

American Medical Industries brochure entitled "Making Your Medications & Vitamins EZ to Swallow", including enclosure entitled Remembering Your Medication Schedule is EZ, published prior to Jun. 7, 1994.
American Medical Industries sales flier entitled "Welcome to American Medical Industries" Family of EZ–Health™ Products, 1993.
Gerber Products Company, Baby Medi–Spoon, 1991.
American Medical Industries Facsimile transmission to Lake Medical Products, Inc. regarding EZ Swallow Pill Crushers & Pill Splitters, Sep. 1, 1993.

*Primary Examiner*—John M. Husar
*Attorney, Agent, or Firm*—Howell & Haferkamp, L.C.

[57] ABSTRACT

Two pill crushing/dispensing cups are provided, with a base cup and a nesting cup being snap-fit together top-to-top which defines a cavity for storing a dosage of pills. By decoupling the cups with the base cup facing upward and inserting the nesting cup therein the pills are crushed/ground between a pair of opposing abraded surfaces. A flange on the exterior of the nesting cup limits the advance of nesting cups such that the opposing abraded surfaces do not mesh. The nesting cup is removed and a liquid is added to the base cup. The cups are again snap-fit together and shaken to facilitate complete suspension of the pill crushings. The cups are decoupled and the suspension is administered directly from either cup.

27 Claims, 2 Drawing Sheets

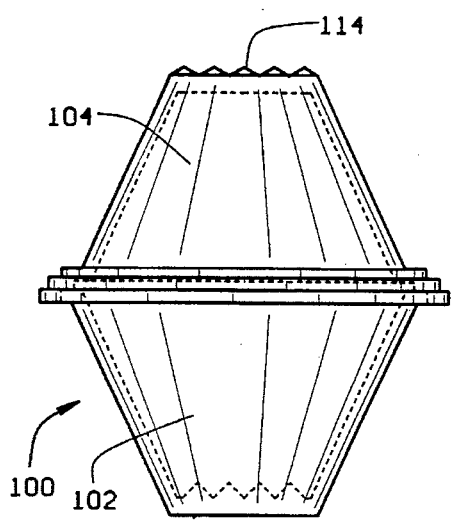
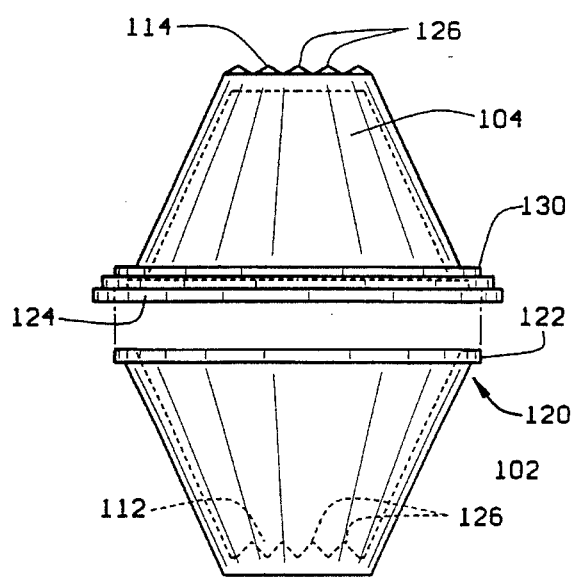
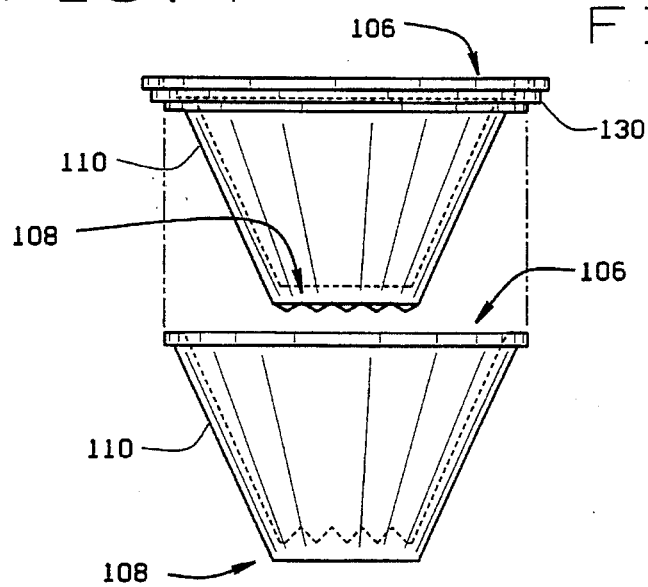
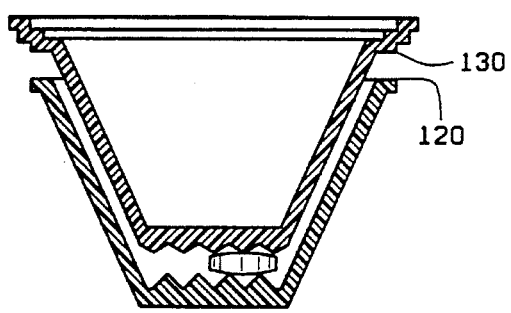
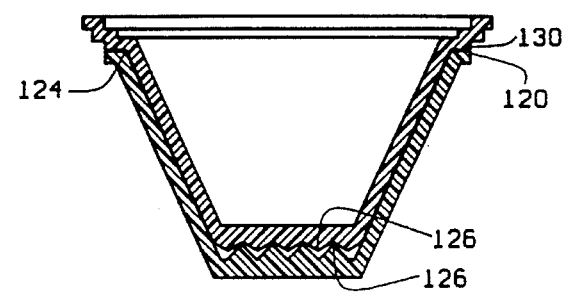

TOP MOUNTED CUPS FOR STORING CRUSHING AND DISPENSING PILLS

CROSS-REFERENCE TO RELATED APPLICATION

This application is a continuation-in-part of Ser. No. 08/288,599 filed Aug. 10, 1994, now U.S. Pat. No. 5,553,793 which is a continuation-in-part of Ser. No. 08/168,019, filed Dec. 15, 1993, now U.S. Pat. No. 5,376,072, the disclosures of which are incorporated herein.

BACKGROUND AND SUMMARY OF THE INVENTION

Administering medication and vitamins, in tablet or capsule form to infants, the elderly, and otherwise feeble hospital patients can be problematic. Not only do these patients have difficulty swallowing the pills, when feeble hospital patients die it is not uncommon for an autopsy to reveal multiple intact pills within the deceased body because the liver failed to produce sufficient enzymes to break through the pill shell. This, of course, prohibits the medication from being dispersed timely into the bloodstream and may contribute to the patient's death. As a result, medication such as aspirin, antibiotics, and other drugs are frequently available in liquid form for easy administration to hospital patients experiencing difficulty with pills and capsules.

For those instances where the medication is only available in pill or capsule form, the pills are frequently crushed in a first container (i.e. with a pestle and mortar), and the pill crushings are then transferred to a second container or dispensing utensil where they can be mixed with a fluid for oral administration to the patient. As detailed in the parent hereto, as cross-referenced above, there are several drawbacks with the pestle and mortar technique such as the risk of low and unpredictable dosage compliance, cross-contamination, and the necessity to purchase and maintain an inventory of multiple utensils and containers for the crushing, mixing, and dispensing tasks. As disclosed and claimed in the parent, the disclosure of which is incorporated herein by reference, a similar problem of administering medication in pill or capsule form exists for comatose and many infirm adult patients physically unable to swallow medication in pill or capsule form. The solution thereto was provided by the pill-crushing syringe disclosed and claimed in the inventor's prior U.S. Pat. No. 5,376,072, noted above. The invention disclosed and claimed therein is a good and valuable invention which itself may be used to crush pills for suspension in a fluid for administration principally through an intravenous tube or the like but which may also be administered orally.

As disclosed in the parent cross-referenced above, the inventors herein have built upon the general pill crushing concept by successfully designing and developing a single use pill dispensing cup with a cup bottom having an abraded surface on its interior and exterior surface. The cup is designed to nest and, when used as a nesting pair, a pill may be placed between an upper and lower cup and crushed between the two abraded surfaces on the interior and exterior of the cup bottoms. Although prior art single use medicine dispensing cups are typically thin walled and flexible, the present invention contemplates a more substantial construction for the cup so as to withstand the force required to crush the pill as the cups are pushed together against the pill and twisted. Additionally, if desired, the cup may have a wider lip to provide a finger grip for the hands as the cups are twisted together.

The abraded surfaces on the interior and exterior surface of each cup bottom are formed from a plurality of pyramidal shaped protrusions with the protrusions having a flatter angle on the exterior surface than on the interior surface. This flatter angle on the exterior surface makes it less likely that pill crushings will be trapped between the protrusions and instead will remain within the bottom cup. After the pill is crushed, fluid is added to the bottom cup to create the suspension which may then be administered. If there are any pill crushings clinging to the exterior surface of the top cup, it may be conveniently "dunked" in the fluid contained in the lower cup and agitated to remove any remaining pill crushings therefrom. This helps to insure high dosage compliance.

After a nested pair are used to crush and administer a pill, they may be conveniently discarded because of their low cost and this eliminates any risk of cross contamination. As a single cup design is used, it may be readily manufactured at high volume using plastics such as polypropylene or polyethylene and thereby produced at a very low cost. Furthermore, the pill crushing feature of the invention is an added bonus and need not be used should the cups be desired simply for dispensing medication as with the prior art cups presently used.

While the pill crushing syringe and the pill crushing/dispensing cups are elegant, simple designs which are amenable to low cost, high volume manufacture, the inventors herein have again built upon the pill crushing concept in order to solve further problems in the prior art and to meet a long felt need. The inventors herein have succeeded in developing a pair of pill crushing cups which enable a pill to be safely stored, crushed, mixed with a liquid, and dispensed directly from one of the cups with minimal risk of contamination and a high degree of dosage compliance.

The cups snap-fit together, top-to-top, defining a cavity therebetween to store a dosage of medication in pill, tablet, or capsule form. The pair of cups includes a base cup, a nesting cup, and a pair of opposing abraded surfaces on the interior and exterior bottom of the base cup and nesting cup, respectively. The snap-fitting feature is achieved by an annular detent adjacent the top of the base cup and an annular recess adjacent the top of the nesting cup for mating with the detent.

To crush the pill(s) stored within the cavity of the cup pair, the snap-fit engagement is decoupled with the base cup facing substantially upward. The nesting cup is nested within the base cup such that the pill is lodged snugly between the opposing abraded surfaces of the base cup and nesting cup. The two cups are pushed and twisted with respect to each other until the pill is crushed and/or ground into fine particles. An annular flange on the outside of the nesting cup engages the rim of the base cup to prevent the abraded surfaces of the base cup and nesting cup from meshing. This allows the particles to be finely crushed/ground by the opposing abraded surfaces, but minimizes the possibility of pill particles being packed within these abraded surfaces which would make a full suspension of the medication more difficult. The nesting cup is then removed and a liquid is added to the base cup for mixing with the pill particles. The abraded surface of the nesting cup may be dipped into the liquid to wash any residual pill crushings therefrom, and the nesting cup is again snap-fit with the base cup. The snap-fit engagement provides a substantial fluid seal which allows the cup pair to be shaken vigorously thereby facilitating rapid and complete suspension of the pill crushings with the liquid. The snap-fit engagement is then decoupled and the suspension may be administered directly from either cup.

While the principal advantages and features of the present invention have been briefly described above, a more thorough understanding and appreciation for the invention's advantages and features may be attained by referring to the drawings and descriptions of the preferred embodiment which follow.

BRIEF DESCRIPTION OF THE DRAWINGS

FIG. 4 is a side elevation view of the two cups of the present invention snap-fit together;

FIG. 5 is a cross-sectional view of the two cups of the present invention better illustrating the annular recess and annular detent;

FIG. 6 is a side elevation view of the nesting cup positioned above the base cup in preparation of nesting therein;

FIG. 7 is a cross-sectional view of the nesting cup within the base cup illustrating a pill lodged between the opposing abraded surfaces; and FIG. 8 is a cross-sectional view of the nesting cup within the base cup illustrating the annular flange of the nesting cup limiting its advance into the base cup.

DESCRIPTION OF THE PREFERRED EMBODIMENT

Figure 1:
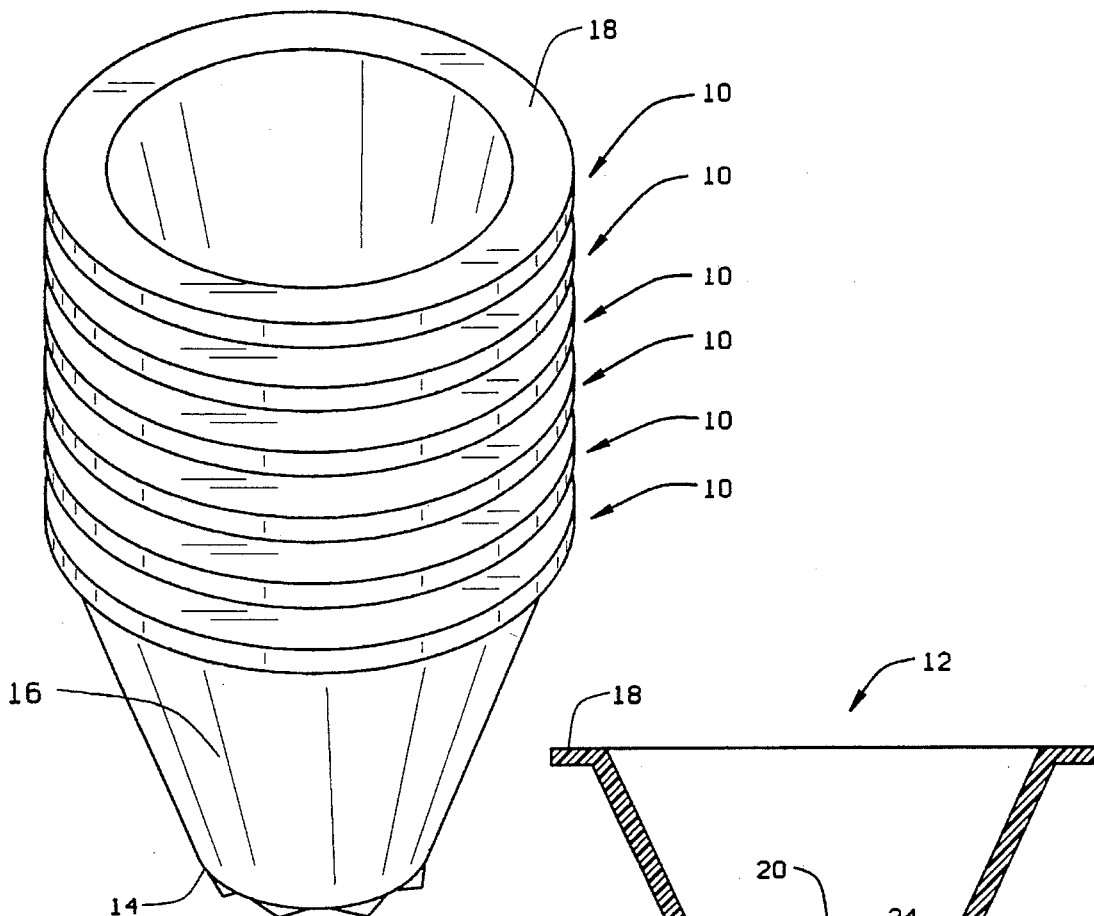
FIG. 1 is an isometric view of a plurality of nested pill crushing/dispensing cups.
Figure 2:
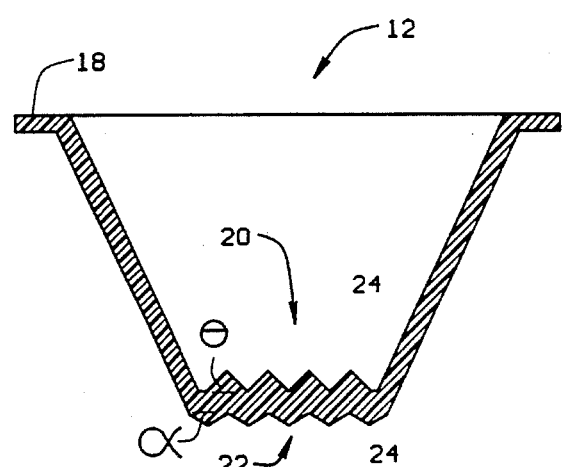
FIG. 2 is a cross-sectional view of one pill crushing/dispensing cup illustrating the interior and exterior abraded surfaces.

A plurality of pill crushing/dispensing cups 10 are illustrated in FIG. 1 stacked atop one another in nested fashion. Each cup includes an open top 12, a closed bottom 14, and a frustoconic wall 16 having a rim 18. The rim 18 is preferably one-quarter inch wide, measured radially, which is sufficiently wide to provide a grip for the fingers to facilitate pushing one of the cups 10 downward into another cup 10. The cups 10 are preferably constructed of styrenic plastic which is light weight but significantly stronger than the cups typical in the prior art. As illustrated in FIG. 2, the bottom 14 includes an interior abraded surface 20 and an exterior abraded surface 22. Alternately, the abraded surfaces may be located at other locations on the cup, such as on the frustoconic wall 16. If located on the side wall 16, the surfaces could conveniently be aligned and a pill crushed therebetween as two cups are nested and twisted against each other. Although preferable, it is not necessary that the pill be crushed as two cups are nested but only that a pill can be crushed by the abraded surfaces.

Preferably, the abraded surfaces 20 and 22 include a plurality of pyramidal shaped protrusions 24 having faces extending from the bottom 14 at an angle θ and α with respect to a horizontal line drawn parallel to the bottom, respectively. In the preferred embodiment the angle θ (interior) is larger than the angle α so that crushed pill particles are less likely to lodge between the protrusions 24 of the exterior abraded surface 22. Preferably θ equals 45° and α equals 30°. Further, the exterior abraded surface 22 includes a protrusion pattern wherein the protrusion tips are level relative to each other (see FIG. 2) and are sufficiently spaced to sturdily support the cup 10 on a tray, cart, table, or other horizontal surface.

Figure 3:
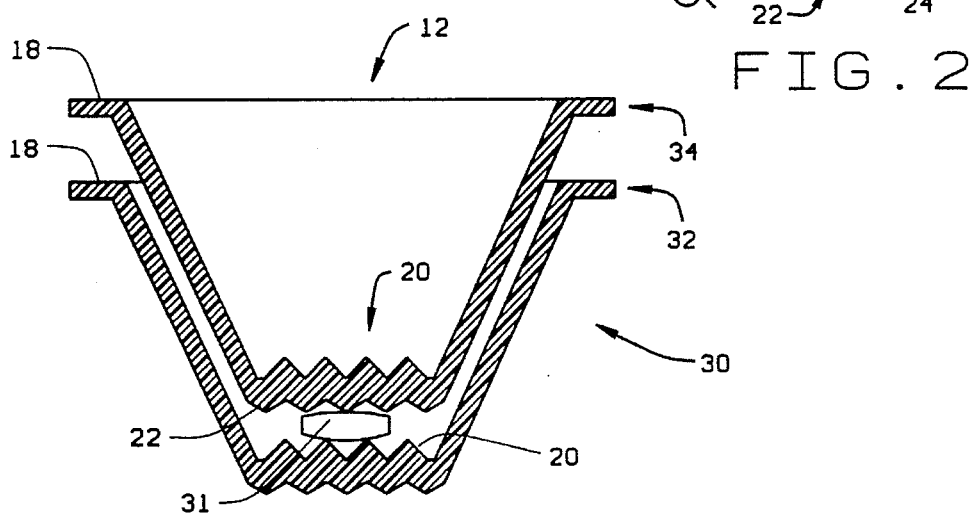
FIG. 3 is a cross-sectional view of a nested pair of the pill crushing/dispensing cups.

This frustoconic design facilitates nesting the cups 10 one atop another thereby allowing large numbers of cups to be stored in a relative small area. FIG. 3 illustrates a nested pair 30 of the cups 10 with a pill 31 positioned therein. The nested pair 30 includes a base cup 32 and a top cup 34 wherein the exterior abraded surface 22 of the top cup 34 is positioned above the interior abraded surface 20 of the base cup 32 when the base cup is positioned upright. Because the cups are designed and manufactured substantially identical to one another, any two cups may be selected from a large supply of the cups 10 to form the nested pair 30.

In operation, a nurse or other health-care professional divides the appropriate quantity of medication to be administered to a given patient and places the pills/capsules in a cup 10 much like the procedure presently used in the prior art to distribute medicated pills and capsules. If a given patient is able to swallow the pills without difficulty, the cup 10 is well suited to perform the function of the flimsy conventional cups utilized by hospitals in the prior art (i.e. merely containing the medication dosage during transport). The level and spaced protrusion pattern on the exterior abraded surface 22 of the cup bottom 14 provides a sturdy foundation for the cup to rest on the medication trays or carts commonly used in the prior art to transport medication to patients' rooms.

However, if a patient requires, or simply desires, the medication to be suspended in a liquid, this elegant cup design easily facilitates such a request. Rather than selecting a single cup 10, the nurse selects a pair of cups. The nested pair 30 is pulled apart and a pill 31 (or a capsule) is placed within the base cup 32. The top cup 34 is repositioned within the base cup 32 such that the pill is lodged snugly between the interior abraded surface 20 of the base cup 32 and the exterior abraded surface 22 of the top cup 34. The cups 32 and 34 are then preferably twisted in opposite directions while being advanced closer together thereby crushing and grinding the pill therebetween. The rim 18 of the top cup 34 provides a convenient finger grip for the hand while pushing and twisting the cups 32 and 34 together. While in an upright position, the top cup 34 is removed from the base cup 32 and a liquid is added to the base cup thereby forming a suspension of the pill crushings. If desired, the bottom of the top cup 34 may be washed off by dipping it into the liquid. This will ensure that virtually all of the pill gets administered to the patient. The suspension is then orally administered directly from the base cup 32.

Because the angle α is preferably only 30°, it is unlikely that any pill crushings will lodge within the exterior abraded surface 22 thereby promoting high-dosage compliance. Moreover, the top cup 34 may be gently tapped against the interior wall of the base cup 32 as it is removed therefrom to further assure that the pill crushings and pill residue are removed from the exterior of top cup 34. While the 45° angle θ may trap a few pill crushings between the interior abraded surface protrusions of the base cup 32, the liquid added to the base cup 32 helps to dislodge any of these pill crushings or residue from the interior abraded surface 20. This, again, contributes to high-dosage compliance. Moreover, this simple design is well adapted for economical mass production thereby making it cost effective to dispose of the top cup 34 and the base cup 32 after only a single use thereby minimizing any risk of cross-contamination.

The inventors have advanced the pill crushing concept by providing a pair of pill crushing cups 100 which snap-fit together as illustrated in FIG. 4. The pair of cups 100 includes a base cup 102 and a nesting cup 104 each having an open top 106, a closed bottom 108, and a frustoconic wall 110. As best shown in FIG. 8, the angle of the frustoconic wall of the base cup may be different than that of the nesting cup to facilitate "wiggling" of the two cups as a pill is crushed. The base cup 102 includes an abraded surface 112 on the interior of its closed bottom and the nesting cup 104 includes an abraded surface 114 on the exterior of its closed bottom. As illustrated in FIG. 5, the base cup includes a rim 120 having an annular detent 122 adapted to mate with an annular recess 124 adjacent the top of the nesting cup 104. The detent 122 and recess 124 enable the pair of cups to snap-fit together top-to-top and provide a substantial fluid seal therebetween. When the cups are snap-fit together, a cavity (not numbered) is defined therein which is suitable for storing pills, tablets, capsules, etc.

Preferably, the abraded surfaces 112 and 114 include a plurality of pyramidal shaped protrusions 126 having faces extending from their respective cup bottoms 108 at an angle between approximately 25° and 45° with respect to a horizontal line drawn parallel to the cup bottom 108. While the nesting cup abraded surface 114 and the base cup abraded surface 112 may form different angles θ and α with respect to the cup bottoms 108 as disclosed above, the precise abraded surface angles are not critical in this embodiment. Experimentation has shown that an angle of approximately 30° for the protrusion patterns 126 of both the nesting cup abraded surface 114 and the base cup abraded surface 112 produces excellent crushing results with a minimum of pill packing and/or residue resulting from the crushing process.

As illustrated in FIGS. 6, 7, and 8, the frustoconic cup design facilitates nesting of the nesting cup 104 within the base cup 102. The nesting cup 104 includes an annular flange 130 around the exterior of its frustoconic wall 110. The flange 130 engages the rim 120 of base cup 102, thereby limiting the advance of the nesting cup 104 into the base cup 102 and preventing the opposing abraded surfaces 112 and 114 from meshing (see FIG. 8). As used herein, the term "mesh" shall mean an arrangement wherein the pyramid protrusions 126 of abraded surfaces 112 and 114 rest flush with each other. Because the flange 130 prohibits the opposing abraded surfaces 112 and 114 from meshing, any packing of the pill particles between the protrusions 126 is minimized and a more complete suspension of pill particles is attained when liquid is added to the base cup. In the preferred embodiment, the flange 130 is positioned such that the tips of the pyramidal protrusions 126 of the opposing abraded surfaces 112 and 114 just meet while the cups are fully nested.

In operation, the pair of cups 100 is provided with a dosage of pills within the cavity defined by the base and nesting cup snap-fit top-to-top as in FIG. 4. The cups so arranged are well-suited for transport as they fit easily into a purse, coat pocket, bag, or other piece of luggage. If the pills are provided directly from a manufacturer/pharmacist, the device 100 may be provided with an adhesive or shrink wrapping to assure that the medication is not contaminated or tampered with before administration. If a person requires, or simply desires the medication within the device 100 to be suspended in a liquid, this elegant design easily facilities such a request. The base cup is positioned upward and the snap-fit engagement is decoupled such that the medication remains in the base cup. This example assumes that a single dosage of medication is stored within the cup pair 100. However, it is understood that multiple dosages may be stored within the cup pair 100. If multiple dosages are present within the cup pair 100, the pills to be administered at a later time are simply removed and temporarily stored as the present dosage is administered.

With the appropriate dosage remaining in the base cup 102, the nesting cup 104 is nested therein such that the pill(s) is lodged between the abraded surfaces 112 and 114 (see FIG. 7). The exterior of the nesting cup open top 106 is sufficiently wide to provide a grip for typical human fingers to facilitate pushing the nesting cup 104 into the base cup 102 and rotating one cup with respect to the other until the pills are crushed/ground into fine particles. The nesting cup 104 is then removed and a liquid is added to the base cup 102 for mixing with the pill crushings. If desired, the nesting cup abraded surface 114 may be washed off by dipping it into the liquid and the cups are then snap-fit together and shaken (vigorously if necessary) to assure that virtually all of the pill crushings are suspended in the liquid. When the cups are snap-fit together, the nesting cup annular recess 124 and the base cup annular detent 122 form a substantial fluid seal sufficient to retain the suspension of pill crushings as the cup pair 100 is shaken. The cup pair 100 is then decoupled and the suspension is orally administered directly from either cup.

Although illustrated embodiments of the present invention are described herein with reference to the accompanying drawings, it is understood that the invention is not limited to those precise embodiments and that various other changes and modifications may be effected therein by one skilled in the art without departing from the scope or spirit of the invention. The scope of the invention is defined solely by the claims, and their equivalents, appended hereto.

What is claimed is:

1. A combination pill storing and crushing device comprising:
 a pair of cups each having an open top and a bottom;
 a releasable coupling for joining the cups top-to-top to thereby create a cavity for storing pills; and
 the cups being nestable such that a pill placed between the cups may be crushed as the two cups are nested.

2. The device of claim 1 wherein the releasable coupling includes a fluid seal between the tops of said pair of cups such that pill crushings and a liquid within the cavity may be shaken while the cups are coupled to facilitate suspension of the pill crushings in the liquid.

3. The device of claim 2 wherein the releasable coupling includes a snap-fit engagement.

4. The device of claim 3 wherein the snap-fit engagement includes an annular detent adjacent the top of one of said cups and an annular recess adjacent the top of the other cup for mating with said detent.

5. The device of claim 4 further including at least one abraded surface on at least one of said cups to facilitate crushing a pill between the cups, adjacent said abraded surface, as the cups are nested.

6. The device of claim 4 wherein the pair of cups includes a base cup and a nesting cup, the base cup having an interior abraded surface positioned to engage an exterior abraded surface on said nesting cup as said cups are nested so that a pill placed between said pair of cups and adjacent said abraded surfaces may be crushed as the cups are nested.

7. The device of claim 6 wherein the nesting cup is rotatable within said base cup to thereby facilitate grinding a pill placed therebetween and adjacent said abraded surfaces.

8. The device of claim 7 wherein the base cup abraded surface and the nesting cup abraded surface are located on the respective cup bottoms.

9. The device of claim 8 further including a mechanical limit to restrict the advance of the nesting cup into the base cup to thereby prevent the opposing abraded surfaces from meshing.

10. A combination pill crushing and dispensing device comprising:

a base cup and a nesting cup nestable within the base cup such that a pill placed between the cups may be crushed as the cups are nested; and a mechanical stop for limiting the advance of the nesting cup into the base cup to thereby prevent the nesting cup from bottoming within the base cup.

11. The device of claim 10 wherein both cups include a frustoconic wall, the base cup includes an open top with a rim therearound, and the mechanical stop includes a flange on the exterior wall of the nesting cup such that the flange meets the rim of said base cup as the nesting cup is fully nested in the base cup to thereby limit further advancement of the nesting cup into the base cup.

12. The device of claim 11 further including at least one abraded surface on at least one of said cups to facilitate crushing a pill between the cups, adjacent said abraded surface, as the cups are nested.

13. The device of claim 12 wherein said at least one abraded surface includes an interior abraded surface on the base cup and an exterior abraded surface on the nesting cup positioned to engage the base cup abraded surface as the two cups are nested so that a pill placed between the two cups and adjacent said abraded surfaces may be crushed as the cups are nested.

14. The device of claim 13 wherein both cups include a bottom and the abraded surfaces are located on the respective cup bottoms.

15. The device of claim 14 wherein the mechanical stop is positioned to limit the advance of said nesting cup to a point which prevents the abraded surfaces from meshing as the cups are nested.

16. A combination pill storage, crushing, and dispensing device comprising:

a base cup and a nesting cup each having an open top and a bottom, and at least one abraded surface on at least one of said cups;

a detent for releasably coupling the base cup and the nesting cup top-to-top creating a cavity within which at least one pill may be stored;

the nesting cup being nestable within the base cup such that a pill may be crushed between the cups, adjacent the abraded surface, as the cups are decoupled and nested; and said detent providing a fluid seal between the tops of said cups so that a liquid mixed with pill crushings may be shaken while the cups are recoupled top-to-top to facilitate suspension of the pill crushings in the liquid.

17. The device of claim 16 wherein said at least one abraded surface includes an abraded surface on the inside of the base cup bottom positioned to engage an abraded surface on the outside of the nesting cup bottom so that a pill placed between the cups, adjacent the abraded surfaces, may be crushed as the cups are nested.

18. The device of claim 17 further including a flange to limit the advance of the nesting cup within the base cup to thereby prevent meshing of the abraded surfaces.

19. The device of claim 18 wherein the nesting cup is rotatable within the base cup to facilitate grinding a pill placed therebetween and adjacent the abraded surfaces.

20. The device of claim 18 wherein both cups include a frustoconic wall and the flange is located on the exterior wall of the nesting cup such that the flange meets a rim at the top of said base cup as the cups are nested to thereby limit further advance of the nesting cup within the base cup before the abraded surfaces mesh.

21. A method of storing at least one pill within a cavity defined by two cups coupled top-to-top, crushing the pill, and dispensing the pill crushings suspended in a fluid, the method comprising the steps of:

decoupling the two cups such that said pill remains within a first of the cups;

crushing the pill by nesting the cups with the pill therebetween;

adding a fluid to the first cup thereby suspending the pill crushings therein; and dispensing the suspension from the first cup.

22. The method according to claim 21 further including the steps of recoupling the second cup with the first cup after the fluid is added to the first cup and shaking the two cups thereby facilitating rapid suspension of the pill crushings with the fluid.

23. A combination pill crushing and dispensing device comprising:

top and bottom cups, said top cup being nestable in said bottom cup, each of said cups having at least one sidewall; and an abraded surface portion on one of said cups;

the sidewall of the top cup being sufficiently rigid so that a crushing force is generated at said abraded surface and against a pill placed between the cups as said top cup is grasped by its sidewall and manually advanced into a nesting configuration with the bottom cup to crush the pill;

the bottom and top cups being shaped and configured so that the inner surface of the sidewall of the bottom cup is closely adjacent the outer surface of the sidewall of the top cup when the cups are nested together.

24. A combination pill crushing and dispensing device as set forth in claim 23 wherein the sidewalls of the cups are tapered.

25. A combination pill crushing and dispensing device as set forth in claim 24 wherein each cup has only one sidewall, the sidewall of each cup being generally circular in transverse cross-section.

26. A combination pill crushing and dispensing device as set forth in claim 25 wherein the sidewall of each cup is generally frusto-conical in shape.

27. A combination pill crushing and dispensing device as set forth in claim 23 wherein each cup has an open top and a bottom, the device further comprising a releasable coupling for joining the cups top-to-top to thereby create a cavity for storing pills.

* * * * *